United States Patent
Hägel et al.

(10) Patent No.: US 6,395,924 B1
(45) Date of Patent: May 28, 2002

(54) T-BUTYLPEROXY-CYCLODODECYL-OXALATE

(75) Inventors: Eberhard Hägel, Icking; Werner Zeiss, Eurasburg; Maximilian Dorn, Pullach, all of (DE)

(73) Assignee: Peroxid-Chemie GmbH & Co KG, Pullach (DE)

( * ) Notice: Subject to any disclaimer, the term of this patent is extended or adjusted under 35 U.S.C. 154(b) by 0 days.

(21) Appl. No.: 09/380,305

(22) PCT Filed: Mar. 4, 1998

(86) PCT No.: PCT/EP98/01215

§ 371 (c)(1),
(2), (4) Date: Aug. 30, 1999

(87) PCT Pub. No.: WO98/39294

PCT Pub. Date: Sep. 11, 1998

(30) Foreign Application Priority Data

Mar. 5, 1997 (DE) .......................... 197 08 982

(51) Int. Cl.[7] ..................... C07C 409/32; C07C 407/00

(52) U.S. Cl. ..................... 560/302; 526/227; 526/232.3; 526/232.5; 560/190; 560/193

(58) Field of Search ................. 560/302, 190, 560/193; 526/227, 232.5, 232.3

(56) References Cited

U.S. PATENT DOCUMENTS 4,455,412 A * 6/1984 Lydiate ........................ 526/227
5,866,712 A * 2/1999 Sanchez ...................... 560/170

FOREIGN PATENT DOCUMENTS

EP 0 095 860 12/1983
EP 0 271 462 6/1988

* cited by examiner

*Primary Examiner*—Fred Zitomer
(74) *Attorney, Agent, or Firm*—Arent Fox Kintner Plotkin & Kahn PPLC

(57) ABSTRACT

The new compound t-butylperoxycyclododecyl oxalate is described, as well as a method of preparing it and use of the compound as a polymerization initiator.

10 Claims, No Drawings

T-BUTYLPEROXY-CYCLODODECYL-OXALATE

SPECIFICATION

This invention relates to the new compound t-butylperoxycyclododecyl oxalate, its production and its use as a polymerization initiator.

For the polymerization of unsaturated monomers, especially of vinyl chloride, there is a need for highly reactive initiators which decompose faster than the peroxydicarbonates most frequently used at present, and which thus allow short reaction cycles even at low polymerization temperatures. Admittedly, there are highly reactive initiators already in use, such as ACSP (acetyl cyclohexane sulfonyl peroxide) and CUPND (cumylperoxy neodecanoate), but these initiators have some disadvantages, eg, unpleasantly smelling decomposition products in the case of CUPND, and corrosive properties in the case of ACSP.

An added disadvantage of highly reactive liquid initiators is the necessity of storing and transporting them at low temperatures, generally below −15° C.

The EP 271 462 (Kenobel AB) describes esters of monoperoxyoxalic acid which are solid at ambient temperature. These esters are the O-n-alkyl, —OO— t-alkyl esters of monoperoxyoxalic acid, where the n-alkyl groups are radicals with 18 to 28 C atoms.

The disadvantage of these compounds is that they are wax-like solids. Their active oxygen content is relatively low on account of the high formula weight (eg, 3.23% in the case of n-docosyl tert-butylperoxy oxalate). They have to be produced from long-chain fatty alcohols which do not dissolve well in the necessary non-polar solvents. One therefore requires large quantities of solvent, which subsequently has to be removed by distillation under vacuum.

Other esters of monoperoxyoxalic acid have also been prepared, which are solid at ambient temperature and, because they have a lower formula weight, have a higher active oxygen content. However, there were safety problems due to the compounds' explosive property and the fact that they are shock sensitive. These undesirable properties are particularly pronounced in the case of bis-tert-butylperoxy oxalate.

The object of this invention consisted in providing an initiator which is solid at ambient temperature and highly reactive when in solution, can be handled safely at temperatures of about +10° C., and which does not have the disadvantages of the hitherto known initiators.

The object is established according to the invention by provision of the new t-butylperoxycyclododecyl oxalate. This compound is a crystalline substance which melts at 48° C., has an active oxygen content of 4.8% and a half-life of 10 hours at 32° C. At 18° C., the loss of active oxygen is about 3% relative in a week, which means that the compound can be handled safely at ambient temperature for a certain length of time.

Surprisingly, t-butylperoxycyclododecyl oxalate turns out to be a highly reactive initiator for the polymerization of unsaturated monomers and in particular for the polymerization of vinyl chloride. It decomposes faster than hitherto known initiators and thus allows short reaction cycles even at low polymerization temperatures of $\leq 50°$ C.

Additional subject matter of the specification is a method of preparing t-butyl-peroxycyclododecyl oxalate. According to this method, t-butylhydroperoxide is reacted with cyclododecyl oxalyl chloride to form the t-butylperoxycyclodo-decyl oxalate. It is preferable if the t-butylperoxycyclododecyl oxalate is obtained as a crystalline compound which, in the form of a solid substance at ambient temperature, is essentially stable and can thus be stored and transported without the need for costly and time-consuming precautions. When the crystalline t-butylperoxycyclododecyl oxalate is dissolved in a suitable solvent, one obtains a solution of a highly reactive initiator with which unsaturated monomers can be polymerized faster than with initiators used so far. During the polymerization of vinyl chloride at 40 to 45° C., the t-butylperoxycyclododecyl oxalate is more reactive than the known initiators CUPND and ACSP.

Also subject matter of the application is the use of t-butylperoxycyclododecyl oxalate as an initiator for the polymerization of unsaturated monomers, in particular of vinyl chloride. However, t-butylperoxycyclododecyl oxalate can also be used as an initiator for other unsaturated monomers, and is suitable, for example, for the production of polyvinyl acetate and LDPE (low-density polyethylene).

The invention is explained in more detail by means of the following examples.

EXAMPLE 1

Preparation of t-butylperoxycyclododecyl oxalate in non-aqueous medium

To a mixture of 800 ml methyl-t-butyl ether, 235 g (=1.2 mol) of an anhydrous 46.2% solution of t-butyl hydroperoxide in petroleum ether (b.p. 40° C.) and 132 g (=1.2 mol) 2.6 dimethyl pyridine, 280 g (=1.0 mol) cyclododecyl oxalyl chloride (98.6% purity) are added dropwise, while stirring and cooling, at a temperature of −5 to 0° C. A viscous suspension forms, which is stirred for a further 45 minutes at 0° C. One adds 600 ml iced water, leaves the mixture to stand for 10 minutes and then separates off the aqueous phase. The organic phase is washed twice with 5% sulfuric acid, using 400 ml of acid each time, and twice with iced water, using 400 ml of water each time.

The solution is cooled to −25° C. and the perester crystallizes out. After filtering, the crystals are washed with a small amount of cold petroleum ether and then dried for 2 hours at 20° C.

One obtains 253 g of a white, finely crystalline powder containing 88% of the desired perester. This corresponds to 68% of the theoretical yield.

EXAMPLE 2

Preparation of t-butylperoxycyclododecyl oxalate in aqueous medium To 800 ml water one adds 6 g of a cationic wetting agent (dimethyl fatty alkyl benzyl ammonium chloride), 254 g (=2.2 mol) 78% aqueous t-butyl hydroperoxide and 242 g (=2.2 mol) 2,6-dimethyl pyridine, cools the mixture to 0° C., and adds 489 g (=1.76 mol) cyclododecyl oxalyl chloride (98.9%) dropwise, while stirring and cooling, over a period of 35 minutes at 0 to +6° C. The reaction mixture is stirred for a further 45 minutes at +6° C., then 600 ml iced water and 90 ml 72% sulfuric acid are added. The solid product is filtered off and washed with iced water until neutral and free of chloride.

One obtains 668 g of a white, finely crystalline, water-damp powder containing 56.7% t-butylperoxycyclododecyl oxalate. This corresponds to 65.5% of the theoretical yield.

EXAMPLE 3

Polymerization of vinyl chloride (VC) with t-butylperoxycyclododecyl oxalate compared to ACSP The t-butylperoxycyclododecyl oxalate (88%) prepared according to Example 1 was tested for its effectiveness as an initiator for the polymerization of vinyl chloride. The test was carried out in a steel autoclave (suspension polymerization) at temperatures of 40° C., 45° C. and 50° C. and for polymerization times of 2 hours, 4 hours and 6 hours. ACSP (acetyl cyclohexansulfonyl peroxide) served as comparative initiator. The results are contained in Table 1, in which CD peroxalate stands for t-butylperoxycyclododecyl oxalate.

| Initiator | T (° C.) | Amount added mmol 100% per-oxide per 70 g VC | Percentage polymerization after | | |
|---|---|---|---|---|---|
| | | | 2 h | 4 h | 6 h |
| CD peroxalate | 40 | 0.12 | 12.1 | 33.2 | 50.8 |
| ACSP | 40 | 0.12 | 8.2 | 21.3 | 35.7 |
| CD peroxalate | 45 | 0.12 | 21.1 | 45.9 | 64.4 |
| ACSP | 45 | 0.12 | 13.3 | 32.1 | 47.8 |
| CD peroxalate | 50 | 0.12 | 29.3 | 48.6 | 56.7 |
| ACSP | 50 | 0.12 | 20.3 | 40.0 | 50.5 |

It is evident from Table 1 that use of the t-butylperoxycyclododecyl oxalate of the invention results in a markedly higher percentage polymerization than does ACSP at the temperatures indicated.

What is claimed is:

1. t-butylperoxycyclododecyl oxalate.

2. A method of preparing t-butylperoxycyclododecyl oxalate, comprising:
   reacting t-butyl hydroperoxide with cyclododecyl oxalyl chloride to form t-butylperoxycyclododecyl oxalate.

3. The method of claim 2,
   wherein the t-butylperoxycyclododecyl oxalate is in a crystalline form.

4. A method for initiating the polymerization of unsaturated monomers comprising:
   mixing an effective amount of t-butylperoxycyclododecyl oxalate with at least one unsaturated monomer to initiate polymerization of the unsaturated monomer.

5. The method of claim 4, wherein the monomer is vinyl chloride.

6. A mixture comprising t-butylperoxycyclododecyl oxalate and an unsaturated monomer.

7. A polymerization initiator consisting essentially of t-butylperoxycyclododecyl oxalate.

8. The initiator of claim 7, wherein the t-butylperoxycyclododecyl oxalate is a crystalline compound.

9. The method of claim 2, further comprising:
   adding cyclododecyl oxalyl chloride dropwise to a non-aqueous hydroperoxide t-butyl solution at a temperature from about −5° C. to about 0 to form a viscous suspension;
   stirring and cooling the viscous suspension;
   thereafter allowing the viscous suspension to stand to form aqueous and organic phases;
   separating the phases, cooling the separated organic phase, filtering the organic phase to obtain crystals; and
   separating the crystals.

10. The method of claim 2, further comprising:
    preparing a mixture of cationic wetting agent, t-butyl hyperoxide and 2,6-dimethyl pyridine in water;
    cooling the mixture;
    adding dropwise cyclododecyl oxalyl chloride while stirring and cooling to obtain a second mixture;
    cooling;
    adding acid; and
    separating the product as a solid, thereby obtaining t-butylperoxycyclododecyl oxalate.

* * * * *